United States Patent
Matyas et al.

(10) Patent No.: US 12,357,470 B2
(45) Date of Patent: Jul. 15, 2025

(54) IMPACTION INSTRUMENT FOR IMPLANTING AN ORTHOPAEDIC KNEE PROSTHESIS AND ASSOCIATED METHOD OF USING THE SAME

(71) Applicant: DePuy Ireland Unlimited Company, Ringaskiddy (IE)

(72) Inventors: Aaron J. Matyas, Fort Wayne, IN (US); Benjamin R. Powers, Columbia City, IN (US); Alasdair J. J. Mercer, Leeds (GB)

(73) Assignee: DePuy Ireland Unlimited Company, Ringaskiddy (IE)

( * ) Notice: Subject to any disclaimer, the term of this patent is extended or adjusted under 35 U.S.C. 154(b) by 403 days.

(21) Appl. No.: 18/082,789

(22) Filed: Dec. 16, 2022

(65) Prior Publication Data
US 2024/0197496 A1 Jun. 20, 2024

(51) Int. Cl.
*A61F 2/46* (2006.01)
*A61F 2/38* (2006.01)

(52) U.S. Cl.
CPC .............. *A61F 2/461* (2013.01); *A61F 2/389* (2013.01); *A61F 2310/00017* (2013.01)

(58) Field of Classification Search
CPC . A61B 17/92; A61B 2017/922; A61F 2/3859; A61F 2/389; A61F 2/461; A61F 2002/4681
See application file for complete search history.

(56) References Cited

U.S. PATENT DOCUMENTS

| | | |
|---|---|---|
| 5,059,196 A | 10/1991 | Coates |
| 5,061,270 A | 10/1991 | Aboczky |
| 5,062,852 A | 11/1991 | Dorr et al. |
| D337,639 S | 7/1993 | Beckman |
| 5,571,111 A | 11/1996 | Aboczky |
| 5,732,992 A | 3/1998 | Mauldin |
| 5,788,701 A | 8/1998 | McCue |
| 5,902,339 A | 5/1999 | Keller |
| 6,520,966 B1 | 2/2003 | Kohler et al. |
| 6,663,636 B1 | 12/2003 | Lin |
| 8,128,703 B2 | 3/2012 | Hazebrouck et al. |
| 8,277,460 B2 | 10/2012 | McMillan et al. |
| 8,317,870 B2 | 11/2012 | Wagner et al. |
| 8,597,302 B2 | 12/2013 | Beedall et al. |

(Continued)

FOREIGN PATENT DOCUMENTS

| | | |
|---|---|---|
| DE | 10013331 A1 | 9/2001 |
| EP | 780090 A1 | 6/1997 |

(Continued)

OTHER PUBLICATIONS

Sigma Fixed Reference Surgical Technique, DePuy Orthopaedics, Inc. 2010, 52 pages.

(Continued)

*Primary Examiner* — Samuel S Hanna
(74) *Attorney, Agent, or Firm* — Barnes & Thornburg LLP

(57) ABSTRACT

An orthopaedic surgical instrument for use during a surgical procedure to implant a tibial tray into a surgically-prepared proximal end of a tibia and a femoral component into a surgically-prepared distal end of a femur is disclosed. The surgical instrument includes a metallic impaction handle and a removable polymeric impaction insert.

8 Claims, 7 Drawing Sheets

(56) References Cited

U.S. PATENT DOCUMENTS

| | | |
|---|---|---|
| 9,039,710 B2 | 5/2015 | Blaylock et al. |
| 9,820,857 B2 | 11/2017 | Wyss et al. |
| 10,092,421 B2 | 10/2018 | Edwards et al. |
| 2003/0109929 A1 | 6/2003 | Keller |
| 2006/0116769 A1 | 6/2006 | Marnay et al. |
| 2006/0200162 A1 | 9/2006 | Farling et al. |
| 2008/0119941 A1 | 5/2008 | Seo et al. |
| 2009/0036909 A1 | 2/2009 | Perry et al. |
| 2011/0301613 A1* | 12/2011 | Green, II ............ A61B 17/921 606/99 |
| 2012/0123429 A1 | 5/2012 | Beedall et al. |
| 2013/0006371 A1 | 1/2013 | Wogoman et al. |
| 2013/0018382 A1 | 1/2013 | Jones et al. |
| 2013/0184829 A1 | 7/2013 | Wyss et al. |
| 2014/0094812 A1 | 4/2014 | Edwards et al. |
| 2014/0094821 A1 | 4/2014 | Wagner et al. |
| 2014/0296929 A1 | 10/2014 | Stacey |
| 2016/0199198 A1 | 7/2016 | Dietz et al. |

FOREIGN PATENT DOCUMENTS

| | | |
|---|---|---|
| WO | 9325164 A1 | 12/1993 |
| WO | 2011004140 A2 | 1/2011 |
| WO | 2011004140 A3 | 4/2011 |

OTHER PUBLICATIONS

Attune Knee System Revision Solutions, Attune Revision Knee System Fixed Bearing Surgical Technique, DePuy Synthes, 2017, 219 pages.

Attune Knee System Intuition Instruments Surgical Technique, DePuy Synthes, 2022, 136 pages.

International Search Report and Written Opinion for International application No. PCT/EP2023/085551, Mar. 11, 2024, 16 pages.

\* cited by examiner

IMPACTION INSTRUMENT FOR IMPLANTING AN ORTHOPAEDIC KNEE PROSTHESIS AND ASSOCIATED METHOD OF USING THE SAME

TECHNICAL FIELD

The present disclosure relates generally to orthopaedic surgical instruments and, more particularly, to surgical instruments used to install an orthopaedic knee prosthesis.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component.

To facilitate the replacement of the natural joint with a prosthesis, orthopaedic surgeons use a variety of orthopaedic surgical instruments such as, for example, impaction handles, cutting blocks, drill guides, and other surgical instruments.

SUMMARY

According to one aspect, an orthopaedic surgical instrument for use during a surgical procedure to implant a component of a knee prosthesis into a surgically-prepared knee bone of a patient includes a polymer impaction insert having a proximal surface and a distal surface that defines an impact surface of an impact head. The impact surface is sized and shaped to be positioned on an outer surface of the component of the knee prosthesis when the impaction insert is used to impact the component of the knee prosthesis. The impaction insert also includes an elongated shaft extending between the proximal surface and the impact head of the impaction insert. An elongated spine extends outwardly from an outer surface of the elongated shaft. The elongated spine extends parallel to a longitudinal axis of the elongated shaft. The surgical instrument also includes a metallic impaction handle removably secured to the impaction insert. The impaction handle has an impact plate that defines a proximal end of the impaction handle. An opposite distal end of the handle has an opening formed therein that is sized and shaped to receive the elongated shaft of the impaction insert. An elongated hollow body extends between the impact plate and the distal end. The elongated hollow body defines an elongated bore. The opening formed in the distal end of the handle opens into the elongated bore. The handle also has an elongated slot that extends parallel to a longitudinal axis of the elongated hollow body. When the impaction handle is secured to the impaction insert, the elongated shaft of the impaction handle is positioned in elongated bore of the impaction handle, and the elongated spine of the impaction insert extends outwardly through the elongated slot of the impaction handle.

In an embodiment, the impact plate has an outer strike surface and an opposite underside surface. The proximal surface of the impaction insert contacts the underside surface of the strike plate when the impaction handle is secured to the impaction insert.

In one embodiment, an annular ring is positioned in the elongated bore of the impaction handle, with the impaction insert having an annular groove defined therein. In such an embodiment, the annular ring of the impaction handle is captured in the annular groove of the impaction insert so as to secure the impaction insert to the impaction handle.

In an embodiment, the component of the knee prosthesis is a tibial tray, and the impact surface of the impact head of the impaction insert is sized and shaped to be positioned on an outer surface of the tibial tray.

In an embodiment, the component of the knee prosthesis is a femoral component, and the impact surface of the impact head of the impaction insert is sized and shaped to be positioned on an outer surface of the femoral component.

In an illustrative embodiment, an outer surface of a portion of the impaction handle between the proximal end and the distal end of the handle defines a grip that is configured to be gripped by a user during impaction of the impact plate. The elongated spine of the impaction insert extends through the grip when the impaction handle is secured to the impaction insert. An outer surface of the elongated spine of the impaction insert may extend beyond the grip of the impaction handle when the impaction handle is secured to the impaction insert.

In an embodiment, the impaction insert is constructed of polyphenylsulfone, and the impaction handle is constructed of stainless steel.

According to another aspect, an orthopaedic surgical instrument for use during a surgical procedure to implant a component of a knee prosthesis into a surgically-prepared knee bone of a patient includes a polymer impaction insert having a proximal surface and a distal surface that defines an impact surface of an impact head. The impact surface is sized and shaped to be positioned on an outer surface of the component of the knee prosthesis when the impaction insert is used to impact the component of the knee prosthesis. The impaction insert also includes an elongated shaft extending between the proximal surface and the impact head of the impaction insert. The surgical instrument also includes a metallic impaction handle removably secured to the impaction insert. The impaction handle has an impact plate defining a proximal end of the impaction handle. The impact plate has an outer strike surface and an opposite underside surface. An opposite distal end of the handle has an opening formed therein that is sized and shaped to receive the elongated shaft of the impaction insert. An elongated hollow body extends between the impact plate and the distal end of the handle. The elongated hollow body defines an elongated bore, with the opening formed in the distal end of the handle opening into the elongated bore. When the impaction handle is secured to the impaction insert, the elongated shaft of the impaction handle is positioned in elongated bore of the impaction handle, and the proximal surface of the impaction insert contacts the underside surface of the strike plate.

In an embodiment, the impaction insert also includes an elongated spine extending outwardly from an outer surface of its elongated shaft. The elongated hollow body of the impaction handle also includes an elongated slot. The elongated spine of the impaction insert extends outwardly through the elongated slot of the impaction handle when the impaction handle is secured to the impaction insert.

In one embodiment, an annular ring is positioned in the elongated bore of the impaction handle, with the impaction insert having an annular groove defined therein. In such an embodiment, the annular ring of the impaction handle is captured in the annular groove of the impaction insert so as to secure the impaction insert to the impaction handle.

In another embodiment, the component of the knee prosthesis is a tibial tray, and the impact surface of the impact head of the impaction insert is sized and shaped to be positioned on an outer surface of the tibial tray.

In an embodiment, the component of the knee prosthesis is a femoral component, and the impact surface of the impact head of the impaction insert is sized and shaped to be positioned on an outer surface of the femoral component.

In an illustrative embodiment, an outer surface of a portion of the impaction handle between the proximal end and the distal end of the handle defines a grip that is configured to be gripped by a user during impaction of the impact plate. The elongated spine of the impaction insert extends through the grip when the impaction handle is secured to the impaction insert. An outer surface of the elongated spine of the impaction insert may extend beyond the grip of the impaction handle when the impaction handle is secured to the impaction insert.

In an embodiment, the impaction insert is constructed of polyphenylsulfone, and the impaction handle is constructed of stainless steel.

According to another aspect, a method of assembling a surgical instrument for use in installing a tibial tray of knee prosthesis onto a surgically-prepared proximal end of a patient's tibia includes determining whether a fixed-bearing tibial tray or a mobile-bearing tibial tray is to be installed onto the surgically-prepared proximal end of the patient's tibia. A fixed-bearing polymer impaction insert is selected if it is determined that a fixed-bearing tibial tray is to be installed onto the surgically-prepared proximal end of the patient's tibia. A mobile-bearing polymer impaction insert is selected if it is determined that a mobile-bearing tibial tray is to be installed onto the surgically-prepared proximal end of the patient's tibia. The selected polymer impaction insert is then secured to a metallic impaction handle such that an elongated shaft of the impaction insert is received into an elongated bore of the impaction handle and an elongated spine extending outwardly from an outer surface of the elongated shaft of the impaction insert extends outwardly through an elongated slot formed in an outer surface of the impaction handle.

In an embodiment, the elongated shaft of the impaction insert is advanced into the elongated bore of the impaction handle such that an annular ring of the impaction handle is captured in an annular groove formed in the impaction insert.

In another embodiment, an outer surface of a portion of the impaction handle between a proximal end and a distal end of the handle defines a grip that is configured to be gripped by a user during impaction of the impact plate, and the elongated spine of the impaction insert extends through the grip when the impaction handle is secured to the selected impaction insert.

In an embodiment, the elongated spine extends outwardly through the elongated slot formed in an outer surface of the impaction handle along a longitudinal axis of the impaction handle.

BRIEF DESCRIPTION OF THE DRAWINGS

The detailed description particularly refers to the following figures, in which.

DETAILED DESCRIPTION OF THE DRAWINGS

Figure 1:
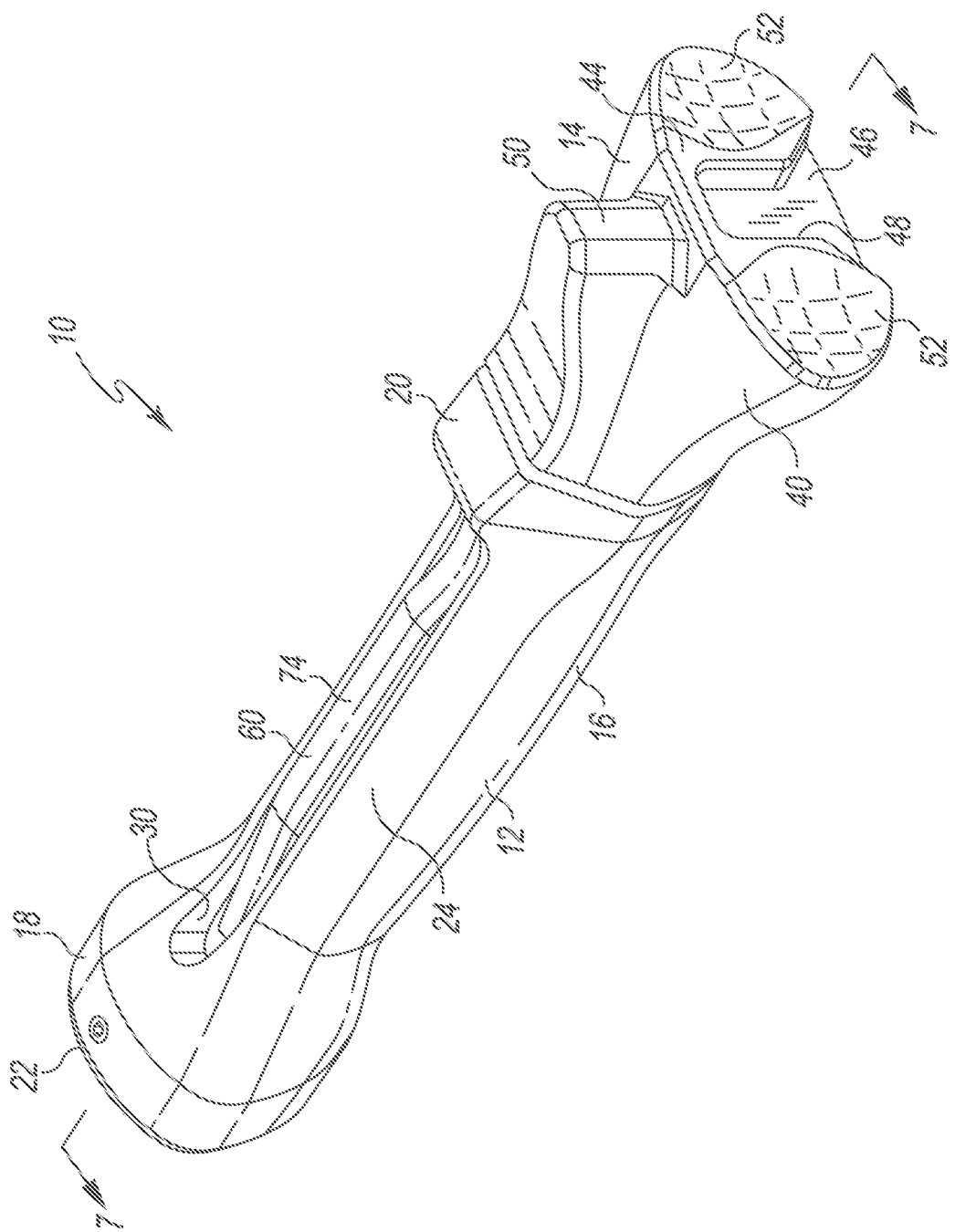
FIG. 1 is a perspective view of an orthopaedic surgical instrument for use in implanting a tibial tray and a femoral component of an orthopaedic knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-4, there is shown an orthopaedic surgical instrument 10 for implanting a tibial tray 200 (see FIG. 8) and a femoral component 250 (see FIG. 9) of a knee prosthesis onto a surgically-prepared proximal end of a patient's tibia and a distal end of a patient's femur, respectively, during an orthopaedic surgical procedure. The orthopaedic surgical instrument 10 includes a metallic impaction handle 12 and a removable polymeric impaction insert 14. As will be discussed below in greater detail, the two-piece design of the surgical instrument 10 allows for certain features of the instrument to be fabricated with differing materials.

Figure 5:
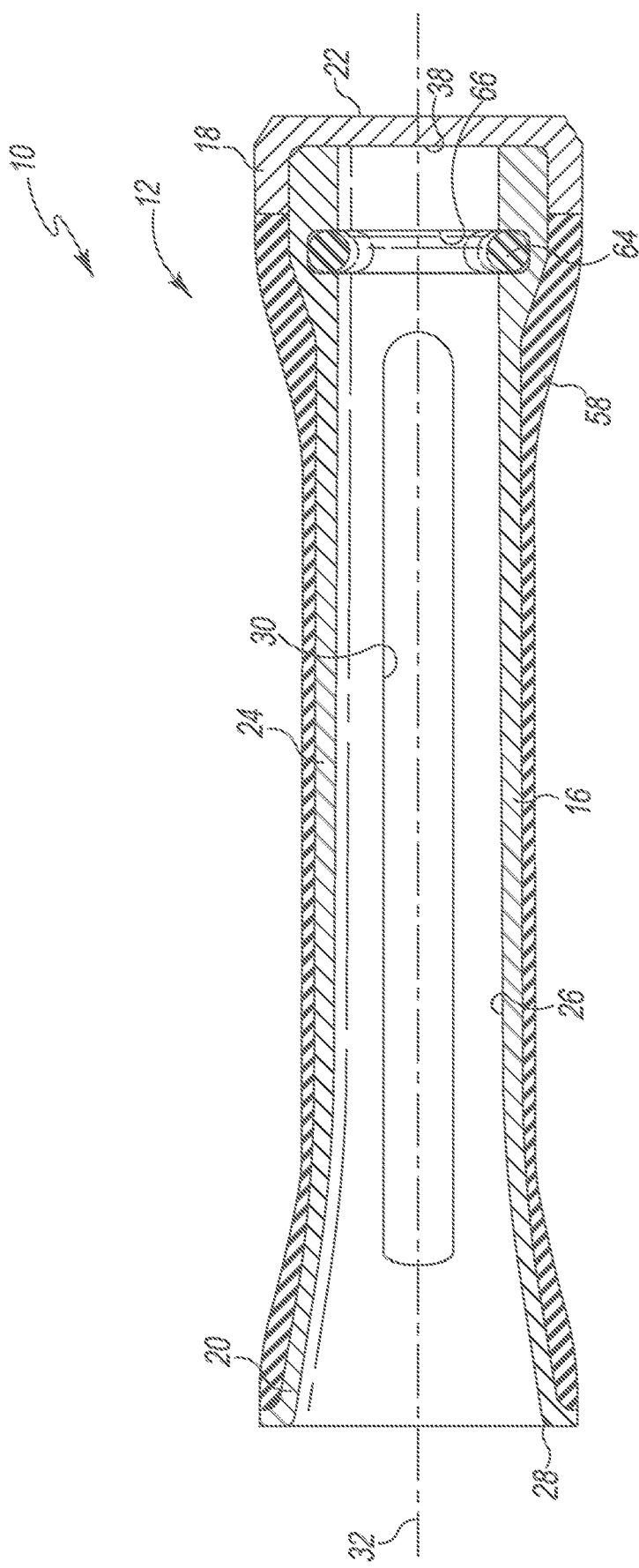
FIG. 5 is a cross-sectional view of the impaction handle taken along the line 5-5 of FIG. 4, as viewed in the direction of the arrows.
Figure 7:
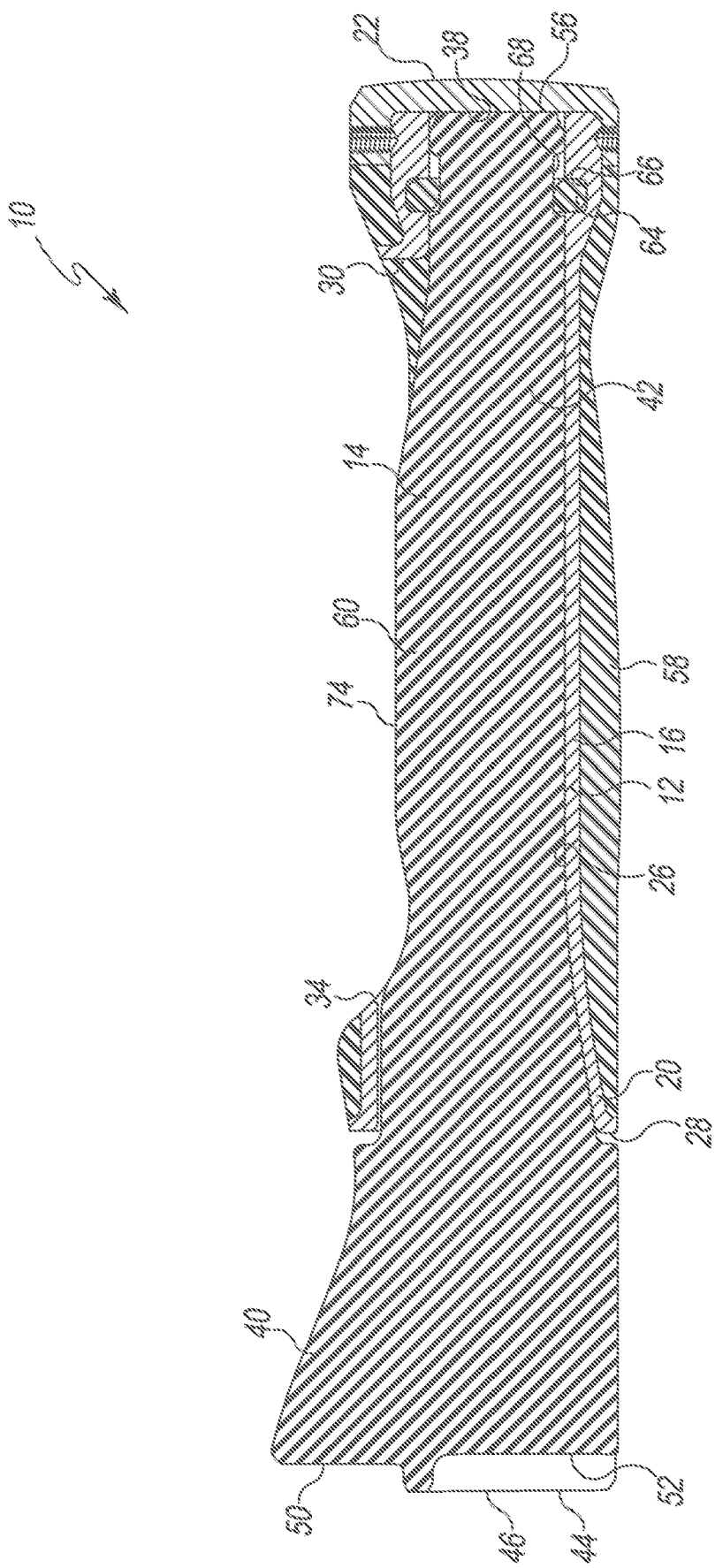
FIG. 7 is a cross-sectional view of the orthopaedic surgical instrument taken along the line 7-7 of FIG. 1, as viewed in the direction of the arrows.

The impaction handle 12 includes an elongated hollow body 16 having an impact plate 18 on its proximal end and a receiver 20 on its distal end. In the illustrative embodiment, the impaction handle 12 is formed from a metallic material such as, for example, stainless steel. In particular, the elongated body 16, the impact plate 18, and the receiver 20 form a metallic assembly assembled from two or more separate components. In particular, as can be seen in FIGS. 5 and 7, the impact plate 18 may be a separate component that is secured to the elongated body 16 via a pair of set screws; although other forms of securing the plate 18 to the body 16, such as welding, may also be used. Moreover, the elongated body 16, the impact plate 18, and the receiver 20 may take the form of a single monolithic metallic component. The impaction handle 12 may be formed by conventional machining techniques, or alternatively, by the use of 3-D printing technology. In the case of 3-D printing, the impaction handle 12 is formed in a layer-by-layer fashion.

In the exemplary embodiment described herein, the impact plate 18 of the impaction handle 12 includes a rounded metal strike surface 22 formed in the proximal end of the impact plate 18. As can be seen in FIG. 5, an opposite underside surface 38 of the impact plate 18 defines the end surface of the handle's elongated blind bore. In use, the surgeon holds the impaction handle 12 via a grip 24 and strikes the strike surface 22 with a surgical mallet, sledge, or other impaction tool to drive the tibial tray 200 into the surgically-prepared proximal end of the patient's tibia or the femoral component 250 into the surgically-prepared distal end of the patient's femur. The impact plate 18 may also be embodied with one or more flanges extending radially outwardly therefrom (not shown). Such flanges serve to protect the surgeon's hand on the grip 24 during impaction.

Figure 3:
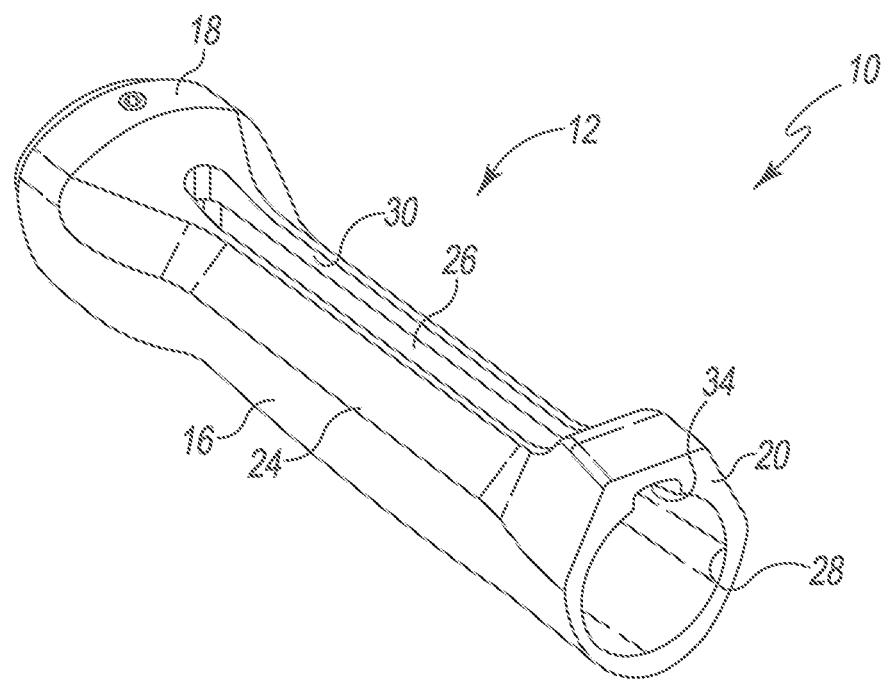
FIGS. 3 and 4 are perspective views of the impaction handle of the orthopaedic surgical instrument of FIG. 1.
Figure 4:
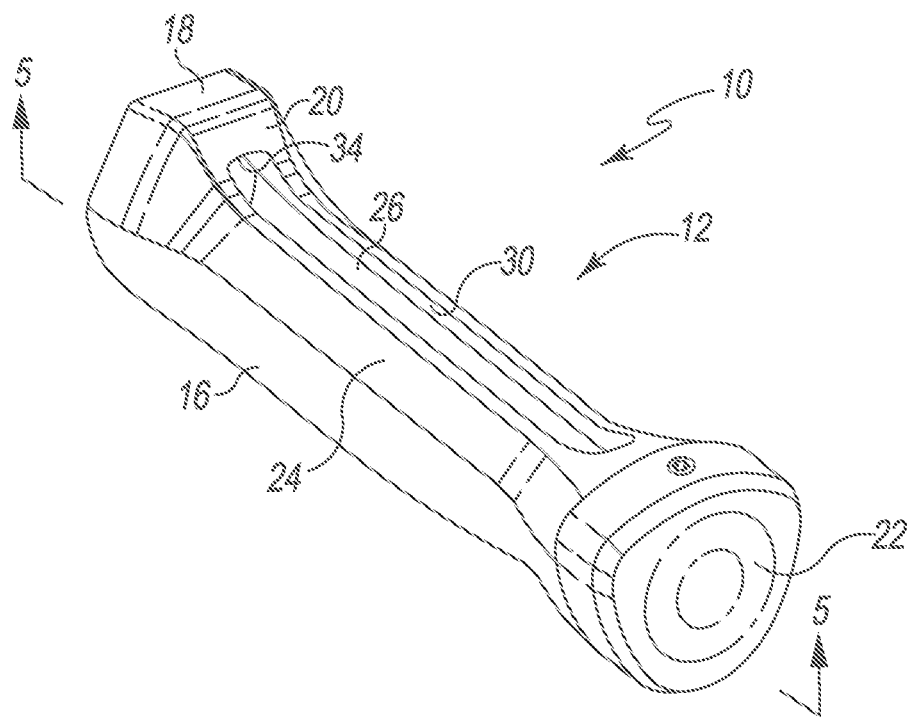

The hollow elongated body 16 of the impaction handle 12 is configured to receive the removable impaction insert 14 of the surgical instrument 10. To do so, the elongated body 16 has a blind elongated bore 26 defined therein. As described in more detail below, the elongated bore 26 is sized and shaped to receive an elongated shaft of the impaction insert 14 therein. As shown in FIGS. 3 and 5, access to the elongated bore 26 is via an opening 28 formed in the distal end of the impaction handle 12. Specifically, as shown in FIG. 5, the opening 28 formed in the handle's receiver 20 opens into the handle's elongated bore 26. As will be described below, the proximal end of the elongated shaft of the impaction insert 14 is advanced through the opening 28 and into the elongated bore 26 during installation of the impaction insert 14 to the impaction handle 12.

As shown in FIGS. 1 and 3-5, the impaction handle 12 has an elongated slot 30 formed therein. In the illustrative embodiment described herein, the elongated slot 30 extends in the direction along the length of the handle 12. In particular, the elongated slot 30 extends in a direction that is parallel to the longitudinal axis 32 of the handle's hollow body 16 (see FIG. 5). In such a way, the elongated slot 30 extends parallel to the bore 26 formed in the elongated body 16. As can be seen in FIG. 5, the elongated slot 30 extends entirely through the handle's body 16 and, as a result, opens into the body's elongated bore 26. As will be described below, an elongated spine formed on the impaction insert 14 extends through the elongated slot 30 when the impaction insert 14 is secured to the impaction handle 12. The impaction handle 12 also has a keying slot 34 formed therein. The keying slot 34 is formed in the handle's receiver 20 and, like the elongated slot 30, it extends parallel to the longitudinal axis 32 of the handle's hollow body 16. The keying slot 34 opens into both elongated slot 30 and the opening 28 formed in the handle's receiver 20. In such a way, it is used to align the impaction insert 14 during installation thereof to the impaction handle 12.

As alluded to above, the outer surface of the portion of the impaction handle 12 between its impact plate 18 and its receiver 20 defines a grip 24. A surgeon or other user grips the grip 24 during use of the surgical instrument 10—e.g., the surgeon grips the instrument via its grip 24 when impacting the impact plate 18. As can be seen in FIG. 1, the elongated slot 30 of the impaction handle 12 is formed in its grip 24. As will be discussed in more detail below, such an arrangement allows the surgeon to make tactile contact with the spine of the impaction insert 14.

As can be seen in FIGS. 5 and 7, the outer surfaces of the handle's elongated body 16, including the grip 24, have a polymeric coating 58 disposed thereon. In the illustrative embodiment described herein, the polymeric coating 58 is embodied as a silicone coating which enhances a surgeon's grip on the surgical instrument 10 during use in a surgical setting in which the instrument may be exposed to fluids.

Figure 8:
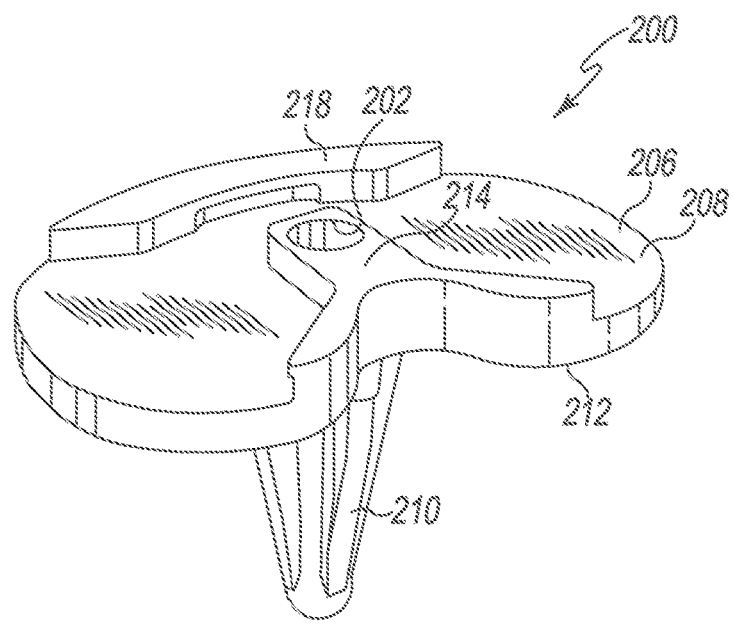
FIG. 8 is a perspective view of a tibial tray of an orthopaedic knee prosthesis.

The impaction insert 14 is configured to engage the tibial tray 200 and the femoral component 250 during implantation of either component 200, 250. As shown in FIG. 8, the tibial tray 200 includes a platform 208 having a fixation member, such as an elongated stem 210, extending away from its inferior surface 212. The elongated tibial stem 210 is configured to be implanted into a surgically-prepared end of a patient's tibia (not shown). A generally Y-shaped posterior buttress 214 extends upwardly from the superior surface 206 of the tibial tray 200. In the illustrative embodiment described herein, the posterior buttress 214 has a pair of arms extending along a posterior section of the perimeter of tibial tray's platform 208, along with a third arm extending anteriorly away from the intersection of such a pair of arms (i.e., in a direction toward the center of the platform 208). As can also be seen in FIG. 8, a superior end of the tray's elongated threaded bore 202 opens into the superior surface of the posterior buttress 214. As further shown in FIG. 8, an arcuate-shaped anterior buttress 218 extends upwardly from the superior surface 206 of the tibial tray 200. The anterior buttress 218 extends along an anterior section of the perimeter of tibial tray's platform 208.

Figure 9:
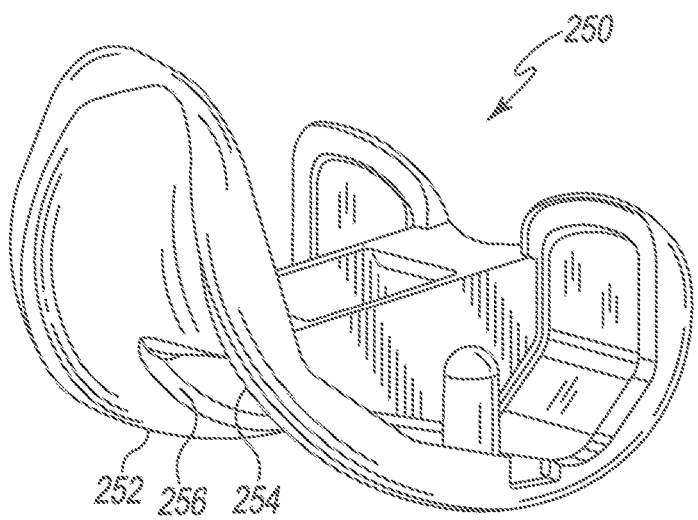
FIG. 9 is a perspective view of a femoral component of an orthopaedic knee prosthesis.

As shown in FIG. 9, the femoral component 250 is configured to be implanted into a surgically-prepared end of the patient's femur (not shown), and is configured to emulate the configuration of the patient's natural femoral condyles. As such, a lateral condyle surface 252 and a medial condyle surface 254 are configured (e.g., curved) in a manner which mimics the condyles of a natural femur. The lateral condyle surface 252 and the medial condyle surface 254 are spaced apart from one another thereby defining an intercondylar notch 256 therebetween.

Figure 6:
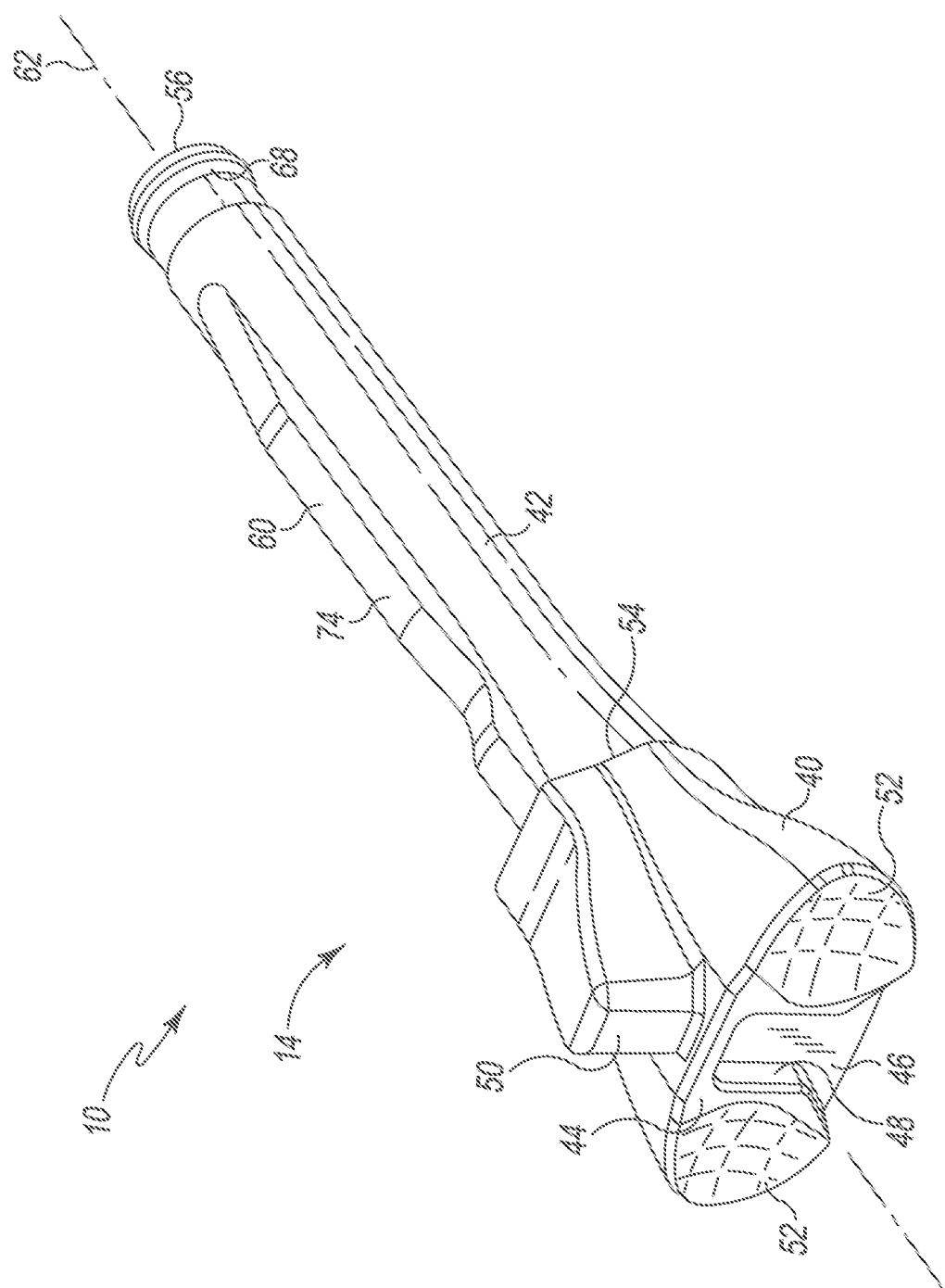
FIG. 6 is a perspective view of the impaction insert of the orthopaedic surgical instrument of FIG. 1.

As shown in FIG. 6, the impaction insert 14 has an impact head 40 with an elongated shaft 42 extending proximally away therefrom. The distal surface 44 of the impaction insert 14 defines an impact surface 46 that is sized and shaped to be selectively positioned on the an outer surface of either the tibial tray 200 or the femoral component 250. In particular, the impact surface 46 of the insert's impact head 40 is sized and shaped to be positioned on the superior surface 206 of the tibial tray 200 (see FIG. 8) when the surgical instrument 10 is used to impact the tibial tray 200 or, alternatively, on the condyle surfaces 252, 254 of the femoral component 250 (see FIG. 9) when the surgical instrument 10 is used to impact the femoral component 250. Specifically, the impact surface 46 includes a generally Y-shaped posterior recess 48 that is sized and shaped to receive the posterior buttress 214 of the tibial tray 200 and an offset shoulder 50 that is sized and shaped to abut the tray's anterior buttress 218. Moreover, the impact surface 46 includes a pair of concave recesses 52 that are sized and shaped to receive the condyle surfaces 252, 254 of the femoral component 250. It should be appreciated that the closely conforming configuration of the insert's impact surface 46 relative to the features of the tibial tray 200 and the femoral component 250 allows for a relatively high impact load transfer efficiency (i.e., impact load transfer efficiency=output force/input force) of the insert.

As shown in FIG. 6, the insert's elongated shaft 42 extends proximally away from the impact head's proximal surface 54. A round, flat proximal surface 56 defines the proximal end of the impaction insert 14. As can be seen in FIG. 6, the impaction insert 14 includes an elongated spine 60 that extends radially outwardly from an outer surface of the insert's shaft 42. In the illustrative embodiment described herein, the spine 60 is arranged parallel to the longitudinal axis 62 of the insert's shaft 42. As shown in FIGS. 1, 2, 6, and 7, the spine 60 has a relatively flat outer surface 74. However, the spine's outer surface 74 may be embodied with ribs, protrusions, peaks, knurling, dimples, or other textures to accommodate the user's grip of the surgical instrument 10. In addition, although the spine 60 is shown in FIGS. 1, 2, 6, and 7 as a single, contiguous structure, it should be appreciated that the spine 60 may be embodied as multiple discreet (i.e., non-contiguous) structures. In other words, the multiple spines may be formed on the insert shaft's outer surface.

Figure 2:
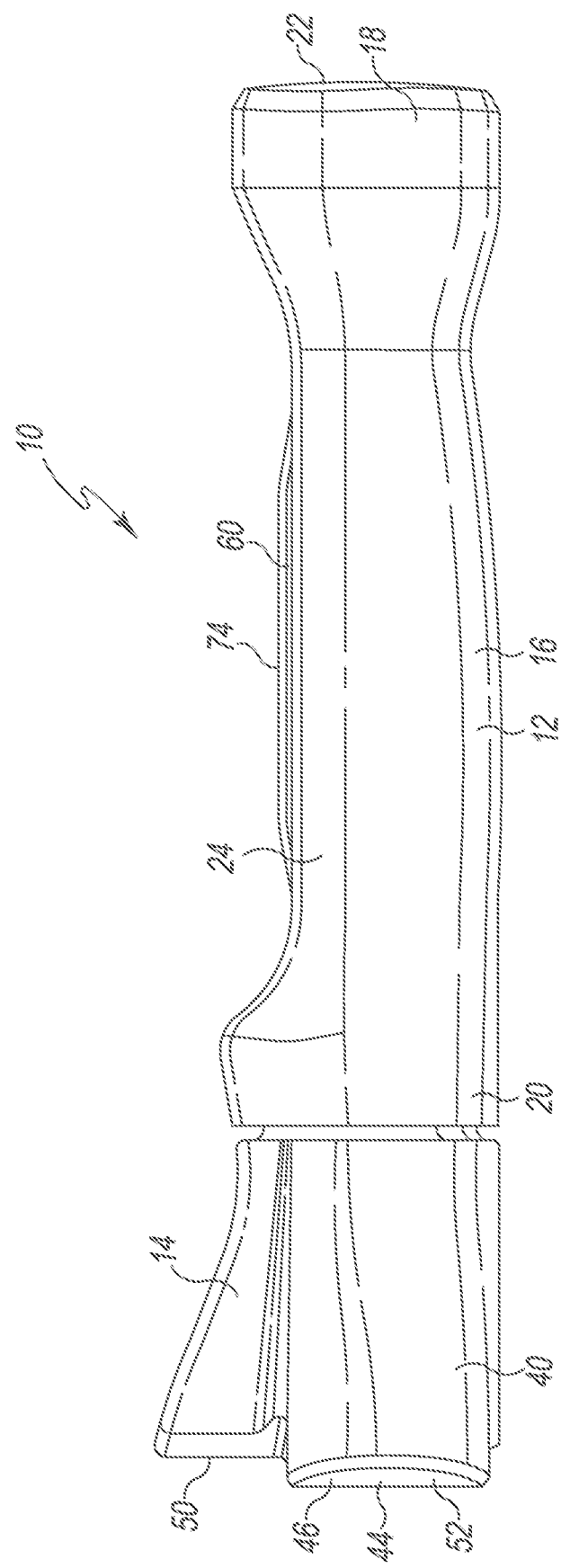
FIG. 2 is an elevation view of the orthopaedic surgical instrument of FIG. 1.

As shown in FIGS. 1, 2, and 7, when the surgical instrument 10 is assembled (i.e., the elongated shaft 42 of the impaction insert 14 is positioned in the elongated bore 26 of the impaction handle 12), the insert's spine 60 extends outwardly through the handle's elongated slot 30. As such, the spine 60 extends outwardly through the handle's grip 24. As can be seen in FIGS. 1, 2, and 7, the height of the spine 60 is such that the spine's outer surface 74 extends beyond the outer surface of the impaction handle 12 defining the grip 24. As such, when a surgeon grips the impaction handle 12, the surgeon's hand also contacts the spine 60 of the impaction insert 14. Such a configuration provides tactile feedback of the insert's impact head 40 to the surgeon during impaction of the surgical instrument 10.

As shown in FIGS. 5 and 7, the elongated bore 26 of the impaction handle 12 has an annular ring 64 positioned therein. The annular ring 64 is positioned in an annular slot 66 formed in the handle's body 16 and may be embodied as any type of retention ring such as, for example, a polymer O-ring, a metallic snap ring, or a ball seal. The annular ring 64 is utilized to removably secure the impaction insert 14 to the impaction handle 12. In particular, as shown in FIGS. 6 and 7, the shaft 42 of the impaction insert 14 has an annular groove 68 formed therein near the shaft's proximal end. The annular ring 64 of the handle 12 may be captured in the annular groove 68 so as to secure the impaction insert 14 to the impaction handle 12. However, a removal force (e.g., pulling force) of sufficient magnitude may be applied to the impaction insert 14 such that the annular ring 64 is freed from the annular groove 68 thereby allowing the impaction insert 14 to be pulled out of, or otherwise removed from, the handle's bore 26. Although the annular ring 64 and the annular groove 66 are shown positioned near the proximal ends of the impaction handle 12 and the impaction insert 14, respectively, it should be appreciated that the location of the ring 64 and the groove 66 may be located at any suitable location along the length of the handle 12 and the insert 14 to fit the needs of a given design. For example, the annular ring 64 and the annular groove 66 may be positioned on the opposite, distal end of the surgical instrument 10. It should also be appreciated that the positions of the annular ring 64 and the annular groove 68 may be swapped to fit the needs of a given design. For example, the annular ring 64 may be positioned on the elongated shaft 42 of the impaction insert 14 with the annular groove 68 being formed in the handle's body 16.

Although the impaction handle 12 is metallic, the impaction insert 14 is embodied as a single monolithic component formed from a polymer material such as, for example, polyphenylsulfone (one suitable polyphenylsulfone is sold under the trademark Radel® and is commercially available from Solvay America, Incorporated of Houston, Texas). The impaction insert 14 may be formed by conventional molding techniques, or alternatively, by the use of 3-D printing technology. In the case of 3-D printing, the impaction insert 14 is formed in a layer-by-layer fashion. The use of differing materials allows the portion of the surgical instrument 10 that is repeatedly impacted by the surgeon (i.e., the impaction handle 12) to be constructed of a fairly hard material (i.e., metal) while also allowing the portion of the instrument that interfaces with the tibial tray 200 and the femoral component 250 (i.e., the impaction insert 14) to be constructed with a softer material (i.e., polymer).

Figure 10:
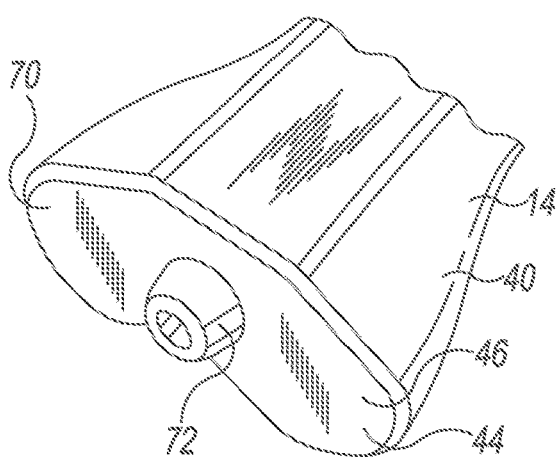
FIG. 10 is a fragmentary perspective view of the impact head of an impaction insert for use in implanting a mobile-bearing tibial tray.

The impaction insert 14 may be provided in differing versions to facilitate implantation of different types of knee components. For example, as shown in FIG. 10, the impaction insert 14 may be configured for use in the installation of a mobile-bearing tibial tray. A mobile-bearing tibial tray is similar to the fixed-bearing tibial tray shown in FIG. 8, except that a mobile-bearing tibial tray does not include either of the buttresses 214, 218, but rather instead the entire superior surface 206 of the tray is planar. As such, the impact surface 46 of the impact head 40 of the impaction insert 14 for use with such a mobile-bearing tibial tray includes a substantially flat surface 70 that conforms with the planar surface of the mobile-bearing tibial tray. As shown in FIG. 10, such an impact surface 46 also includes a locating feature, such as a distally-extending annular protrusion 72, which is received into the bore 202 formed in the mobile-bearing tibial tray to locate the insert's impact head 40 on the tray during impaction.

In use, the impaction handle 12 and the impaction insert 14 may be utilized by a surgeon to implant the tibial tray 200 into the surgically-prepared proximal end of a patient's tibia and/or the femoral component 250 into the surgically-prepared distal end of a patient's femur. To do so, the surgeon first determines whether a fixed-bearing tibial tray or a mobile-bearing tibial tray is to be installed on the proximal end of the patient's tibia. Depending on the type of tibial tray to be installed, the surgeon selects the corresponding type of impaction insert 14 (e.g., either the insert 14 shown in FIG. 6 or the insert 14 shown in FIG. 10) and secures it to the impaction handle 12. To do so, the surgeon inserts the proximal end of the impaction insert 14 into the opening 28 formed in the handle's receiver 20. With the insert's spine 60 aligned with the keying slot 34 formed in the handle's receiver 20, the surgeon advances the shaft 42 of the impaction insert 14 into the handle's bore 26 until the annular ring 64 of the handle 12 is captured in the insert's annular groove 68 thereby securing the impaction insert 14 to the impaction handle 12. When secured in such a manner, the proximal surface 56 of the impaction insert 14 contacts the underside surface 38 of the impact plate 18. Moreover, when secured in such a manner, the insert's spine 60 extends outwardly through the handle's elongated slot 30, and thus outwardly through the handle's grip 24.

Once the surgical instrument 10 is assembled, the surgeon then aligns the instrument's impact head 40 with the knee component positioned on the patient's bone. Specifically, in the case of installation of a fixed-bearing tibial tray, the impact surface 46 of the impaction insert 14 of FIG. 6 is placed on the superior surface 206 of the tibial tray 200 positioned on the patient's proximal tibia such that the tray's posterior buttress 214 is positioned in the insert's posterior recess 48 thereby also positioning the tray's anterior buttress 218 under the impact head's offset shoulder 50. In the case of installation of a mobile-bearing tibial tray, the impact surface 46 of the impaction insert 14 of FIG. 10 is placed on the planar superior surface 206 of the mobile-bearing tibial tray positioned on the patient's proximal tibia such that the impact head's annular protrusion 72 is received into the bore 202 formed in the mobile-bearing tibial tray thereby also positioning the impact head's flat surface 70 on the tray's planar superior surface 206. In the case of installation of the femoral component 250, the impact surface 46 of the impaction insert 14 of FIG. 6 is placed on the condyle surfaces of the femoral component 250 positioned on the patient's distal femur such that the component's condyle surfaces 252, 254 are received into the insert's concave recesses 52.

Thereafter, the surgeon strikes the impact plate 18 of the impaction handle 12 with a surgical mallet, sledge, or other impaction tool to drive the tibial tray 200 into the bone tissue until the tibial tray 200 is fully seated on the patient's surgically-prepared proximal tibia (in the case of the tibial tray) or drive the femoral component 250 into the bone tissue until the femoral component is fully seated on the patient's surgically-prepared distal femur (in the case of the femoral component).

If so desired, the surgeon may then remove the impaction insert 14 from the impaction handle 12 by pulling on the insert 14 with a removal force (e.g., pulling force) of sufficient magnitude such that the annular ring 64 of the handle is freed from the annular groove 68 of the insert thereby allowing the impaction insert 14 to be pulled out of, or otherwise removed from, the handle's bore 26.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, it should be appreciated that the concepts described herein may be utilized in the design of impaction handles for use in implanting other types of orthopaedic implants such as hip implants, shoulder implants, or other components (e.g., femoral) of a knee prosthesis.

Moreover, in a further illustrative embodiment, the annular ring 64 of the handle 12 and the annular groove 68 of the insert 14 may be configured to create a pneumatic seal. In conjunction with such a pneumatic seal, the proximal surface 56 of the impaction insert 14 is spaced apart from the underside surface 38 of the impact plate 18 thereby functioning as a pneumatic piston within the pneumatic cylinder created by the sealed area within the handle's bore 26. In such an arrangement, pneumatic dampening is provided during impaction by the pressurized air within the sealed area within the handle's bore 26.

Yet further, the distal end of the handle's hollow body 16 may be modified to provide audible feedback to the surgeon. In particular, a number of slots may be formed in the receiver 20 of the handle 12 so as to create vibratory resonating sound similar to that of a tuning fork. Such a sound may be tuned by the number and locations of the slots formed in the receiver 20, the length and width of such slots, and/or the type of slots (e.g., open or closed). When tuned to a desired arrangement, the generated audible sound will change based on the type of strike (the amount of energy put in and if square or not), but also based on the amount of resistance/compliance of the implant component (e.g., tibial tray or femoral component) on the bone (this is a product of the bone/material density and the amount of interference). As such, the audible sound generated during a strike may give feedback to the surgeon as the implant component progresses. In particular, at an early stage of implantation, the implant component is relatively easily progressing into the bone without much resistance and, as a result, produces a vibratory resonating sound that is different than when the implant component is in its final movements toward being fully seated and thus experiencing a relatively high amount of resistance. This progressive change in the audible feedback provided to the surgeon is a function of the reflective reaction force and reflective impulse wave changes as the implant component is advanced into the bone. It should also be appreciated that such feedback isn't provided to the surgeon solely as audible feedback, but rather the progressive vibration amplification provides a tangible and progressive vibratory feedback to the surgeon's hand.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An orthopaedic surgical instrument for use during a surgical procedure to implant a component of a knee prosthesis into a surgically-prepared knee bone of a patient, comprising:
   a polymer impaction insert having (i) a proximal surface, (ii) a distal surface that defines an impact surface of an impact head, the impact surface being sized and shaped to be positioned on an outer surface of the component of the knee prosthesis when the impaction insert is used to impact the component of the knee prosthesis, (iii) an elongated shaft extending between the proximal surface and the impact head of the impaction insert, and (iv) an elongated spine extending outwardly from an outer surface of the elongated shaft, the elongated spine extending parallel to a longitudinal axis of the elongated shaft, and
   a metallic impaction handle removably secured to the impaction insert, the impaction handle having (i) an impact plate defining a proximal end of the impaction handle, (ii) an opposite distal end having an opening formed therein that is sized and shaped to receive the elongated shaft of the impaction insert, (iii) an elongated hollow body extending between the impact plate and the distal end, the elongated hollow body defining an elongated bore, the opening formed in the distal end opens into the elongated bore, and (iv) an elongated slot extending parallel to a longitudinal axis of the elongated hollow body,
   wherein when the impaction handle is secured to the impaction insert (i) the elongated shaft of the impaction insert is positioned in the elongated bore of the impaction handle, and (ii) the elongated spine of the impaction insert extends outwardly through the elongated slot of the impaction handle.

2. The orthopaedic surgical instrument of claim 1, wherein:
   the impact plate having an outer strike surface and an opposite underside surface, and
   the proximal surface of the impaction insert contacts the underside surface of the strike plate when the impaction handle is secured to the impaction insert.

3. The orthopaedic surgical instrument of claim 1, wherein:
   an annular ring is positioned in the elongated bore of the impaction handle, the impaction insert has an annular groove defined therein, and the annular ring of the impaction handle is captured in the annular groove of the impaction insert so as to secure the impaction insert to the impaction handle.

4. The orthopaedic surgical instrument of claim 1, wherein:

the component of the knee prosthesis comprises a tibial tray, and the impact surface of the impact head of the impaction insert being sized and shaped to be positioned on an outer surface of the tibial tray.

5. The orthopaedic surgical instrument of claim 1, wherein:

the component of the knee prosthesis comprises a femoral component, and the impact surface of the impact head of the impaction insert being sized and shaped to be positioned on an outer surface of the femoral component.

6. The orthopaedic surgical instrument of claim 1, wherein:

an outer surface of a portion of the impaction handle between the proximal end and the distal end of the handle defines a grip that is configured to be gripped by a user during impaction of the impact plate, and the elongated spine of the impaction insert extends through the grip when the impaction handle is secured to the impaction insert.

7. The orthopaedic instrument of claim 6, wherein an outer surface of the elongated spine of the impaction insert extends beyond the grip of the impaction handle when the impaction handle is secured to the impaction insert.

8. The orthopaedic surgical instrument of claim 1, wherein:

the impaction insert is constructed of polyphenylsulfone, and the impaction handle is constructed of stainless steel.

* * * * *